(12) United States Patent
Quezada

(10) Patent No.: US 6,582,736 B2
(45) Date of Patent: Jun. 24, 2003

(54) THERAPEUTIC OIL COMPOSITION

(75) Inventor: Richard S. Quezada, West Hills, CA (US)

(73) Assignee: Terra de Sol, West Hills, CA (US)

( * ) Notice: Subject to any disclaimer, the term of this patent is extended or adjusted under 35 U.S.C. 154(b) by 0 days.

(21) Appl. No.: 10/094,400

(22) Filed: Mar. 8, 2002

(65) Prior Publication Data

US 2002/0136788 A1 Sep. 26, 2002

Related U.S. Application Data

(60) Provisional application No. 60/278,134, filed on Mar. 23, 2001.

(51) Int. Cl.[7] .............................................. A61K 35/78
(52) U.S. Cl. ....................... 424/742; 424/745; 424/747; 424/757
(58) Field of Search ................................ 424/742, 747, 424/745, 757

(56) References Cited

PUBLICATIONS

Lawless, J. The Illustrated Encyclopedia of Essential Oils: The Complete Guide to the Use of Oils in Aromatherapy and Herbalism. 1995. Element Books, Boston, pp 50, 51, 141, 162, 175, 177, 180, 181 and 223.*

Hoffman, D. The Complete Illustrated Herbal: A Safe and Practical Guide to Making and Using Herbal Remedies. 1996. Barnes & Noble, Inc., Italy, pp 28–29.*

* cited by examiner

Primary Examiner—Christopher R. Tate
Assistant Examiner—Michele C. Flood
(74) Attorney, Agent, or Firm—Kelly Bauersfeld Lowry & Kelley, LLP

(57) ABSTRACT

A therapeutic oil composition is provided that is useful for topical application to painful areas of the human body. The therapeutic oil composition is created by mixing essentials oils of *Eugenia caryophyllata, Myroxylon balsamum* var. *pereirae, Eucalyptus globulus* var. *globulus, Lavandula augustifolia, Mentha piperita,* and *Mentha spicata.* The volume of each constituent added can be modified according to the desired treatment. The mixture is then aged by storing it in the dark at a temperature of between 50° F. to 60° F. for at least thirty-six hours. The composition may be applied topically in 100% strength, or mixed with an oil-based carrier, and allowed to enter through the skin and into the tissue to relieve complaints of physical pain, including muscular aches and pains, arthritis and respiratory distress.

22 Claims, No Drawings

THERAPEUTIC OIL COMPOSITION

RELATED APPLICATION

This application claims priority from U.S. provisional application No. 60/278,134, filed Mar. 23, 2001.

BACKGROUND OF THE INVENTION

The present invention generally relates to alternative therapies for physical pain. More particularly, the present invention relates to a composition of six essential oils forming a therapeutic composition for the temporary relief of various body complaints.

For thousands of years, many cultures of humanity have looked across their world and sought remedies for disease. From the four corners of this planet they have developed therapeutic medicines from the very plants, trees, flowers and even the roots themselves. In the days of ancient Egypt, Papyrus manuscripts dating back 2800 BC recorded the use of hundreds of medicinal herbs, fine oils and perfumes. The Egyptians held many of these essential oils in high regard due to their therapeutic properties. When the Greeks visited Egypt, they learned a great deal regarding the medicinal applications of aromatic plants. The father of medicine, Hippocrates, prescribed fumigations and fomentations. Megallus himself created a famous preparation, made from myrrh, cinnamon and cassis. This was used both as a perfume and as a remedy for skin inflammation and battle wounds.

Plants and herbs have long been used for medicinal purposes. Indeed, Native Americans have long known of the healing powers of certain herbs as remedies for various illnesses. Well known examples of using plants and herbs for medicinal purposes include aspirin, which comes from the bark of a white willow tree, and digitalis, which comes from a flower commonly known as Foxglove.

The Arabs produced many great men of science, among them Avicenna (980–1037 AD). Of his many fine works and discoveries, he invented the refrigerated coil, a breakthrough in the art of distillation, which he used to produce essential oils. During these times, there was an outlook possessed by these inventors, a common interest in the interrelatedness of matter and spirit. They used their intuition with the known sciences of their day.

As the Renaissance period came and went, so did the role of essential oils for direct therapeutic intervention. With the arrival of technical chemistry, synthetic counterparts of essential oils created the modern drug industry. They reduced the role of essential oils to employment in perfumes, cosmetics and foods.

In these modern times, pain management is of great concern for those who are prescribed various drugs. Side effects and toxicity are very real experiences mounting negative evidence of these synthetic versions.

Accordingly, there is a need for a natural oil composition which can be used for physical therapy in treating pain and other human body ailments. The present invention fulfills this need and provides other related advantages.

SUMMARY OF THE INVENTION

The present invention resides in a composition of six essential oils extracted from various plants, trees, flowers and roots. More particularly, eugenia caryophyllata, myroxyon pereira, eucalyptus globulus, lavandula augustifolia, mentha piperita, and mentha spicata oil. These constituents are typically added between approximately 8% and 25% by volume of the total composition volume. In a particularly preferred embodiment, the six constituents are each about ⅙ by volume of the total composition volume. These constituents are mixed and blended to create a singular blend.

The mixture is then aged by storing the mixture in the dark for at least a predetermined time period. Preferably, the mixture is stored at a temperature of between 50° F. to 60° F. for at least thirty-six hours.

The therapeutic composition of the present invention may be then topically applied to the afflicted area, the amount of a dosage typically administered by drops or a spray mechanism. Alternatively, the composition is mixed with a carrier, which is typically oil-based. The carrier may comprise at least one of: vegetable oil, apricot kernel oil, avocado oil, borage oil, canola oil, evening primrose oil, grape seed oil, hazelnut oil, jojoba oil, *rosa musceta* oil, wheat germ oil, soy bean oil and sweet almond oil. In such carrier, the composition is applied topically to the afflicted area as a balm.

As a fast acting remedy, this invention acts with relief to the painful area. As a 100% natural product, the invention is a safe, non-toxic alternative and without the side effects of pharmaceutical medicines prescribed for physical pain.

Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

The present invention resides in a therapeutic composition that provides a safe, effective therapeutic alternative for pain management. It consists of six carefully chosen essential oils. These oils are then blended and aged to a formula that is the basis of the invention. This invention has a pleasant fragrance, soothing to all skin conditions and performs well for many painful complaints.

The composition comprises six essential oils, namely:

1) *Eucalyptus Globulus* Var. *Globulus* (Eucalyptus);
2) Eugenia Caryophyllata (Clove Bud);
3) *Myroxylon Balsamum* Var. *Pereirae* (Peru balsam)
4) *Mentha Spicata* (Spearmint);
5) *Mentha Piperita* (Peppermint); and
6) *Lavandula Augustifolia* (True Lavender).

The oils are 100% pure in strength. The botanical oils are typically extracted via steam, water or dry distillation. This process isolates only the volatile and water-insoluble parts of the plant. Essential oils are usually liquid, but can also be solid (orris) or a semi-solid (rose). They dissolve in pure alcohol, fats and oils but not in water and, unlike the so-called fixed plant oils (such as olive oil), they evaporate when exposed to air, leaving no oily residue.

The following is a description of the individual components, their principal active constituents, and their actions and indications based on past use and history.

1) *Eucalyptus Globulus*—Eucalyptus

PRINCIPAL CONSTITUENTS—Cineol (70–85%), pinene, limonene, cymene, Phellandrene, terpinene, aromadendrene, among others.

ACTIONS—Analgesic, antieuralgic, antirhueumatic, antiseptic, antispasmodic, antiviral, balsamic, cicatrisant, decongestant, deodorant, depurative, diuretic, expectorant, febrifuge, hypoglycemic, rebefacient, stimulant, vermifige, vulnerary INDICATIONS—Muscular aches and pains, arthritis, rheumatism, asthma, bronchitis, colds, fevers, flu, infectious illnesses, headaches, neuralgia.

2); *Eugenia Caryophyllata*—Clove Bud

PRINCIPAL CONSTITUENTS—Eugenol (60–90%), eugenol acetate, Caryophyllene.

ACTIONS—Anthelminthic, antibiotic, anti-emetic, antihistaminic, antirheumatic antineuralgic, antioxidant, antiseptic, antiviral, carminative, counter irritant, Expectorant, larvicidal, spasmolytic, stimulant, stomachic, vermifuge.

3) *Myroxylon balsamum* var. *pereirae*—Peru balsam

PRINCIPAL CONSTITUENTS—Cinnamein (50–64%), resin (20–28 percent) benzoic and cinnamic acid esters such as benzyl benzoate, benzyl cinnamate, and cinnamyl cinnamate and other traces.

ACTIONS—Anti-inflammatory, antiseptic, balsamic, expectorant, stimulant, and promotes the growth of epithelial cells.

INDICATIONS—Rheumatism, asthma, bronchitis, low blood pressure, colds, dry skin, eczema, rashes, sores, bruises, nervous tension, stress.

4) *Mentha spicata*—Spearmint

PRINCIPAL CONSTITUENTS—L-Carvone (50–70%), dihydrocarvone, Phellandrene, limonene, menthone, menthol, pulegone, cineol, linadol, pinenes.

ACTIONS—Anesthetic (local), antiseptic, antispasmodic, astringent, carminative, cephalic, cholagogue, decongestant, digestive, diuretic, expectorant, febrifuge, hepatic nervine, stimulant, stomachic, tonic.

INDICATIONS—Stress, headache, migraine, nervous strain, neurasthenia, colds, flu, fevers, colic, dyspepsia, flatulence, hepatobiliary disorders, nausea, vomiting, asthma, bronchitis, catarrhal conditions, sinusitis.

5) *Mentha piperita*—Peppermint

PRINCIPAL CONSTITUENTS—Menthol (29–48%) Menthone (20–31%) Menthyl acetate, menthofuran, limonene, pulegone, cineol, among others.

ACTIONS—Analgesic, anti-inflammatory, antimicrobial, antiphlogistic, antipruritic, Antiseptic, antispasmodic, antiviral, astringent, carminative, cephalic, cholagogue, cordial, emmenagogue, expectorant, febrifuge, hepatic, nervine, stomachic, sudorific, vasoconstrictor, vermifuge.

INDICATIONS—Neuralgia, muscular pain, palpitations, asthma, bronchitis, sinusitis, dermatitis, toothache, scabies, spasmodic cough, colic, cramps, dyspepsia, flatulence, colds, flu, fevers, fainting, mental fatigue, migraine, nervous stress, vertigo.

6) *Lavandula augustifolia*—True lavender

PRINCIPAL CONSTITUENTS—More than 100 constituents including linalyl acetate (40%) linadol, lavandulol, lavandulyl acetate, terpineol, cineol, limonene, ocimene, caryophyllene, among others.

ACTIONS—Analgesic, anti-convulsive, antidepressant, antimicrobial, antirheumatic, antiseptic, antispasmodic, antitoxic, carminative, cholagogue, choleretic, cicatrizznt, cordial, cytophylactic, diuretic, emmenagogue, hypotensive, nervine, sedative, stimulant, sudorific, tonic, vermifuge, vulnerary.

INDICATIONS—Lumbago, muscular aches and pains, rheumatism, sprains, asthma, bronchitis, catarrh, laryngitis, throat infections, whooping coughs, bruises, burns, wounds, inflammations, insect bites and strings, abdominal cramps, colic, dyspepsia, flatulence, nausea, flu, depression, headaches, hypertension, insomnia, migraine, nervous tension and stress related conditions, shock, PMS, sciatica, vertigo.

The geographic location in which the plant deriving the oil is grown can be important to the present invention. For example, lavendar produced in a nursery in Los Angeles would produce a less potent oil than the lavendar grown along the French Alps. Therefore, there is an importance to the soil, weather, altitude and other conditions that affect the potency of the oil derived from the plant. Accordingly, the myroxylon balsamum is preferably obtained from plants grown in Peru. The clove oil is preferably obtained from India, the eucalyptus from China, lavendar from France, and spearmint and peppermint oils from the United States. While these oils are preferably obtained from the geographic locations indicated, the invention is not necessarily limited to such, as each oil may be obtained from different sources, although the degree of potency may vary.

The composition of the present invention is formed by combining each of the aforementioned named essential oils. Preferably, the amount of each essential oil is in equal proportion. For example, to create one liquid ounce of the composition, ⅙th of an ounce of each essential oil is divided then blended equally. However, it is to be understood that the ratio may vary by plus or minus 50% of any of the named essential oils in order of specific requirements. The symptoms and location of pain will determine the amounts of each essential oil within the overall ratio. For example, if an indication is tooth ache, the amount of peppermint (mentha piperita) may be increased up to 50%. Thus, each constituent oil can be added to the composition by volume of approximately 8% to 25% of the total composition volume.

The blended composition of these essentials oils are then aged. It has been found that as time passes, say four months, the compositional blend seems to increase in potency, much like a fine wine that ages with time. A sufficient aging period for this composition has been found to be between thirty-six to forty-eight hours. The mixture composition blend needs to amalgamate without disturbing. Preferably, the mixed composition is stored in a dark room having a temperature between 50° F. to 60° F.

Although the composition may be applied in its 100% pure strength, this is not necessary and the composition is often incorporated into carriers which may be a liquid, gel, or ointment, and typically oil-based. Preferable oil-based carriers include: vegetable oil, apricot kernel oil, avocado oil, borage oil, canola oil, evening primrose oil, grapeseed oil, hazelnut oil, jojoba oil, rosa musceta oil, wheatgerm oil, soybean oil, and sweet almond oil. As some of these oils have been used by themselves for certain indications, the composition may be combined with that particular oil for enhanced effectiveness due its symbiotic effect. The ratio of the composition to the carrier oil is determined by the skin condition and the location of pain.

When in liquid form, the composition is applied with the use of a dropper or the like. Preferably, the number of these drops is in multiples of seven. For more severe cases of pain, the amount is increased by a multiple of seven drops. A pump sprayer may be screwed onto a bottle that accomplishes the method of application while providing less waste and more control to the area of need. Preferably, the composition is stored within an opaque bottle (such as a cobalt blue or deep violet glass bottle) so as not to be adversely affected by outdoor or indoor light, in order to preserve the quality of the compositional blend. In any event, the composition is to be only administered topically. The composition enters through the skin and into the muscular tissue. Within minutes, this non-toxic, non-irritating, non-sensitizing remedy travels through the blood system, providing a wholesome, enabling effect to the afflicted area.

The present invention has been tested with overwhelming results, providing an alternative therapy for relief of pain and other afflictions. Examples of such trials and tests will now be described.

EXAMPLES OF TREATMENT

Arthritis 48 yr old mother of two suffering from chronic arthritic hip pain—left side. Applied composition to the region several time per day, resulting in relief of this pain within one week.

68 yr old male semi-truck driver suffering from chronic arthritic pain of his left hand fingers. Applied composition to the region once, resulting in complete relief.

50 yr old male suffering from a right shoulder arthritic pain. Sprayed composition to the area three times a day for one week, resulting in complete relief.

Asthma/Chronic Obstructive Pulmonary Disease (COPD)/Bronchitis/Coughs/Laryngitis/Throat Infections 72 yr old female suffering from a chronic asthmatic condition. Sprayed composition to the area within her room—once. Resulting in the freedom to breathe freely for the first time in years.

56 yr old female suffering from severe COPD. Applied composition to her upper chest area three times a day for two days. Resulting in fifty per cent relief, with a freedom to breath easier.

12 yr old girl suffering from a throat infection with cough. Applied composition to the frontal area of her throat—twice in one day. Resulting in complete relief.

Flu/Fever/Muscular Aches and Pains 10 yr old girl suffering from a bout with the flu. Applied composition to the navel area twice in one day. Resulting in over night recovery.

55 yr old male suffering from chronic lower back pain resulting in sleepless Nights. Applied composition to the area once. Resulting in a sound sleep and no pain.

34 yr old mother suffering from severe left shoulder pain caused by a serious car accident. Unable to sleep due to intense pain with no relief from the medications prescribed by her doctors. Applied composition to the area several times over two days. Resulting in a total relief of the pain.

Although several embodiments have been described in detail for purposes of illustration, various modifications may be made without departing from the scope and spirit of the invention. Accordingly, the invention is not to be limited, except as by the appended claims.

What is claimed is:

1. A method for creating a therapeutic oil composition, comprising the steps of:
   mixing essential oils of *Eugenia caryophyllata, Myroxylon balsamum* var. *pereirae, Eucalyptus globulus* var. *globulus, Lavandula augustifolia, Mentha piperita,* and *Mentha spicata;* and
   aging the mixture.

2. The method of claim 1, wherein the essential oils of *Eugenia caryophyllata, Myroxylon balsamum* var. *pereirae, Eucalyptus globulus* var. *globulus, Lavandula augustifolia, Mentha piperita,* and *Mentha spicata* are each between approximately 8% and 25% by volume of the total composition volume.

3. The method of claim 2, wherein the essential oils of *Eugenia caryophyllata, Myroxylon balsamum* var. *pereirae, Eucalyptus globulus* var. *globulus, Lavandula augustifolia, Mentha piperita,* and *Mentha spicata* are each about ⅙ by volume of the total composition volume.

4. The method of claim 1, wherein the aging step includes the step of storing the mixture in the dark for at least a predetermined time period.

5. The method of claim 4, wherein the aging step further includes the step of storing the mixture at a temperature of between 50° F. to 60° F.

6. The method of claim 1, wherein the predetermined time period is 36 hours.

7. The method of claim 1, including the step of mixing the composition with a carrier.

8. The method of claim 7, wherein the carrier is oil-based.

9. The method of claim 8, wherein the carrier comprises at least one of:
   vegetable oil, apricot kernel oil, avocado oil, borage oil, canola oil, evening primrose oil, grapeseed oil, hazelnut oil, jojoba oil, rosa musceta oil, wheatgerm oil, soybean oil, and sweet almond oil.

10. A method for creating a therapeutic oil composition, comprising the steps of:
    mixing essential oils of *Eugenia caryophyllata, Myroxylon balsamum* var. *pereirae, Eucalyptus globulus* var. *globulus, Lavandula augustifolia, Mentha piperita,* and *Mentha spicata* each between approximately 8% and 25% by volume of the total composition volume; and
    aging the mixture by storing the mixture in the dark and at a temperature of between 50° F. to 60° F. for at least 36 hours.

11. The method of claim 10, wherein the essential oils of *Eugenia caryophyllata, Myroxylon balsamum* var. *pereirae, Eucalyptus globulus* var. *globulus, Lavandula augustifolia, Mentha piperita,* and *Mentha spicata* are each about ⅙ by volume of the total composition volume.

12. The method of claim 10, including the step of mixing the composition with a carrier.

13. The method of claim 12, wherein the carrier is oil-based, and selected from at least one of:
    vegetable oil, apricot kernel oil, avocado oil, borage oil, canola oil, evening primrose oil, grapeseed oil, hazelnut oil, jojoba oil, rosa musceta oil, wheatgerm oil, soybean oil, and sweet almond oil.

14. A therapeutic oil composition, consisting essentially of:
    essential oils of *Eugenia caryophyllata, Myroxylon balsamum* var. *pereirae, Eucalyptus globulus* var. *globulus, Lavandula augustifolia, Mentha piperita,* and *Mentha spicata*.

15. The composition of claim 14, wherein the essential oils of *Eugenia caryophyllata, Myroxylon balsamum* var. *pereirae, Eucalyptus globulus* var. *globulus, Lavandula augustifolia, Mentha piperita,* and *Mentha spicata* are each between 8% and 25% by volume.

16. The composition of claim 15, wherein the essential oils of *Eugenia caryophyllata, Myroxylon balsamum* var. *pereirae, Eucalyptus globulus* var. *globulus, Lavandula augustifolia, Mentha piperita,* and *Mentha spicata* are each ⅙ by volume.

17. The composition of claim 14, including a carrier.

18. The composition of claim 17, wherein the carrier is oil based and selected from at least one of:
    vegetable oil, apricot kernel oil, avocado oil, borage oil, canola oil, evening primrose oil, grapeseed oil, hazelnut oil, jojoba oil, rosa musceta oil, wheatgerm oil, soybean oil, and sweet almond oil.

19. The composition of claim 14, wherein the composition is aged.

20. A therapeutic oil composition, consisting essentially of:
   an aged mixture of essential oils of *Eugenia caryophyllata, Myroxylon balsamum* var. *pereirae, Eucalyptus globulus* var. *globulus, Lavandula augustifolia, Mentha piperita,* and *Mentha spicata* each between 8% and 25% by volume; and
   an oil-based carrier.

21. The composition of claim 20, wherein the essential oils of *Eugenia caryophyllata, Myroxylon balsamum* var. *pereirae, Eucalyptus globulus* var. *globulus, Lavandula augustifolia, Mentha piperita,* and *Mentha spicata* are each $\frac{1}{6}$ by volume.

22. The composition of claim 20, wherein the carrier is selected from at least one of:
   vegetable oil, apricot kernel oil, avocado oil, borage oil, canola oil, evening primrose oil, grapeseed oil, hazelnut oil, jojoba oil, rosa musceta oil, wheatgerm oil, soybean oil, and sweet almond oil.

* * * * *